US008849068B2

(12) United States Patent
Abe et al.

(10) Patent No.: US 8,849,068 B2
(45) Date of Patent: Sep. 30, 2014

(54) IMAGE MANAGEMENT SYSTEM, IMAGE MANAGEMENT METHOD, AND PROGRAM

(75) Inventors: Masahiro Abe, Yokohama (JP); Keiichi Sakai, Kawasaki (JP); Koji Takekoshi, Yokohama (JP); Naoki Yamada, Hatogaya (JP)

(73) Assignee: Canon Kabushiki Kaisha, Tokyo (JP)

( * ) Notice: Subject to any disclaimer, the term of this patent is extended or adjusted under 35 U.S.C. 154(b) by 1206 days.

(21) Appl. No.: 11/387,738

(22) Filed: Mar. 24, 2006

(65) Prior Publication Data
US 2006/0239395 A1    Oct. 26, 2006

(30) Foreign Application Priority Data

Apr. 8, 2005    (JP) ................................. 2005-112654

(51) Int. Cl.
| | | |
|---|---|---|
| G06K 9/00 | (2006.01) |
| G06K 9/40 | (2006.01) |
| G06K 9/54 | (2006.01) |
| G06K 9/60 | (2006.01) |
| G06F 7/00 | (2006.01) |
| G06F 12/00 | (2006.01) |
| G06F 17/30 | (2006.01) |
| A61B 5/05 | (2006.01) |
| G01N 23/04 | (2006.01) |

(52) U.S. Cl.
CPC ...................................... G01N 23/04 (2013.01)
USPC ........... 382/305; 382/128; 382/254; 707/610; 707/821; 600/407

(58) Field of Classification Search
USPC .................. 382/100, 128–132, 305, 254; 707/821–831, 610; 711/154–166; 600/300, 407, 408
See application file for complete search history.

(56) References Cited

U.S. PATENT DOCUMENTS 6,006,231 A  * 12/1999 Popa ...................................... 1/1
6,574,629 B1 *  6/2003 Kaufman et al. ..................... 1/1
(Continued)

FOREIGN PATENT DOCUMENTS

JP         3014372 A       1/1991
JP         08263625      * 10/1996
(Continued)

OTHER PUBLICATIONS

Office Action dated Mar. 16, 2012 in corresponding Japanese Application No. 2006-068276.

*Primary Examiner* — Randolph I Chu
*Assistant Examiner* — Nathan Bloom
(74) *Attorney, Agent, or Firm* — Fitzpatrick, Cella, Harper & Scinto

(57) ABSTRACT

An image management system, image management method and program are provided that can favorably manage images for displaying images that underwent optimization processing or images for creating and displaying difference images in which the generation of artifacts is suppressed. An image from image generator 100 is input to server 109 and stored in storage device 105. The system then determines whether an image including attendant information that is the same as that of the input image is already registered in the system. When such an image is not already registered, attendant information included in the input image is read out and newly registered in association with the input image. In contrast, when an image including attendant information that is the same as that of the input image is registered in the system and the attendant information is registered, information indicating the fact that the image was input is registered.

8 Claims, 7 Drawing Sheets

(56) References Cited

U.S. PATENT DOCUMENTS

| | | | |
|---|---|---|---|
| 6,782,137 B1* | 8/2004 | Avinash | 382/254 |
| 6,909,795 B2* | 6/2005 | Tecotzky et al. | 382/128 |
| 7,043,066 B1* | 5/2006 | Doi et al. | 382/132 |
| 7,054,473 B1* | 5/2006 | Roehrig et al. | 382/128 |
| 7,545,967 B1* | 6/2009 | Prince et al. | 382/130 |
| 2001/0011336 A1* | 8/2001 | Sitka et al. | 711/161 |
| 2001/0022862 A1* | 9/2001 | Alm | 382/305 |
| 2002/0151781 A1* | 10/2002 | Ohishi et al. | 600/407 |
| 2002/0158875 A1* | 10/2002 | Yamada | 345/440 |
| 2004/0008900 A1* | 1/2004 | Jabri et al. | 382/254 |
| 2004/0071369 A1 | 4/2004 | Onishi | |
| 2004/0101188 A1* | 5/2004 | Oosawa | 382/132 |
| 2004/0120606 A1* | 6/2004 | Fredlund | 382/305 |
| 2004/0122787 A1* | 6/2004 | Avinash et al. | 706/50 |
| 2005/0111733 A1* | 5/2005 | Fors et al. | 382/173 |
| 2005/0113961 A1* | 5/2005 | Sabol et al. | 700/182 |
| 2005/0157916 A1* | 7/2005 | Sato | 382/130 |
| 2005/0203954 A1* | 9/2005 | Abe | 707/104.1 |
| 2005/0262089 A1* | 11/2005 | Wu | 707/10 |
| 2005/0267351 A1* | 12/2005 | Humphrey et al. | 600/408 |
| 2006/0242144 A1* | 10/2006 | Esham et al. | 707/6 |
| 2007/0076929 A1* | 4/2007 | Gentles et al. | 382/128 |
| 2008/0279439 A1* | 11/2008 | Minyard et al. | 382/131 |

FOREIGN PATENT DOCUMENTS

| | | | |
|---|---|---|---|
| JP | 8315119 A | | 11/1996 |
| JP | 2001-266147 | | 9/2001 |
| JP | 2003052679 A | | 2/2003 |
| JP | 2004097651 A | | 4/2004 |
| JP | 2004097652 A | | 4/2004 |
| JP | 2005039701 A | * | 2/2005 |
| JP | 2005051702 A | | 2/2005 |

* cited by examiner

F I G. 5

| IMAGE ID | PROCESSED | BEFORE PROCESSING | PATH |
|---|---|---|---|
| 012345 | 1 | 0 | ¥abc¥001¥012345.dcm |
| 123579 | 0 | 1 | |
| 421573 | 1 | 1 | ¥def¥004¥421573.dcm |

| IMAGE ID | PROCESSED | BEFORE PROCESSING | PATH |
|---|---|---|---|
| 012345 | 1 | 0 | ¥abc¥001¥012345.dcm |
| 123579 | 0 | 1 | |
| 421573 | 1 | 1 | ¥def¥004¥421573.dcm |
| 421580 | 0 | 1 | |

| IMAGE ID | PROCESSED | BEFORE PROCESSING | PATH |
|---|---|---|---|
| 012345 | 1 | 0 | ¥abc¥001¥012345.dcm |
| 123579 | 0 | 1 | |
| 421573 | 1 | 1 | ¥def¥004¥421573.dcm |
| 421580 | 1 | 1 | ¥def¥004¥421580.dcm |

71

IMAGE MANAGEMENT SYSTEM, IMAGE MANAGEMENT METHOD, AND PROGRAM

FIELD OF THE INVENTION

The present invention relates to an image management system, an image management method and a program for conducting radiogram interpretation observations in the field of medical treatment.

BACKGROUND OF THE INVENTION

Currently, various inspection apparatuses such as a plain X-ray apparatus, CT (Computerized Tomography) and MRI (Magnetic Resonance Imaging) exist in the field of medical treatment, and "diagnostic imaging" that performs diagnosis using images obtained from these inspection apparatuses is actively performed. For example, radiogram interpretation observation is performed in which a physician carries out a radiogram interpretation by comparing a plurality of radiation images that were imaged in time sequence for a disease site of a patient, to thereby grasp the state of progress or state of healing of an affected area and consider the treatment policy.

Monitor diagnosis is also being carried out that displays images output from an imaging apparatus as digital data on a monitor such as a liquid crystal display to perform diagnosis, and this is replacing the conventional method in which film that was imaged is hung on a projector to perform diagnosis. Thus, by handling images as digital data it has become possible to perform various kinds of diagnosis that were not possible with the conventional film, such as changing the gradation and magnifying or reducing an image at the time of diagnosis.

In recent years, with the object of improving the efficiency of radiogram interpretations or enhancing the radiogram interpretation performance with respect to radiogram interpretation observations performed by physicians, a method has been proposed that performs an inter-image operation, beginning with differential processing (subtraction), between images as comparison objects to highlight differences between the images. Highlighting the differences between images makes it possible to prevent errors caused by oversights by the radiogram interpreter.

Although this inter-image operation (subtraction) is generally performed after aligning structures that appear in each image, even when the structures are completely aligned there are cases in which the signal values for the density or brightness or the like of the corresponding structures among both images do not match. Therefore, in some cases artifacts arise in the images obtained by the inter-image operation, due to this signal value difference.

In general, images obtained from an imaging apparatus are not originally acquired for the purpose of an inter-image operation, and each image is independently reproduced as a visible image that is suitable for radiogram interpretation observation. Therefore, each image is optimized in accordance with optimization conditions that are set respectively for each image. In particular, since images that were imaged at different stages in a time series are obtained by performing optimization for each image, uniform optimization is not performed for all of the images. Accordingly, in most cases the signal values for the density or brightness of the structures as described above do not match, and even if an inter-image operation is performed for these kinds of images there is a high possibility that artifacts will arise.

In order to solve the above described problem, a system has been proposed that can carry out a higher precision inter-image operation by performing image processing so as to make each image an image that in suitable for an inter-image operation (see Japanese Patent Laid-Open No. 2001-266147).

However, according to the method described in Japanese Patent Laid-Open No. 2001-266147, there is a problem that a large amount of processing time is required to perform image processing to make images into images suitable for an inter-image operation. There is thus a need for a system that can perform the above described inter-image operation in a shorter time and, furthermore, acquire images with few artifacts.

SUMMARY OF THE INVENTION

The present invention was made in view of the above circumstances and an object of the present invention to provide an image management system, image management method and program that can favorably manage images for displaying images which underwent optimization processing or images for creating and displaying difference images in which the generation of artifacts is suppressed.

Another object of the present invention is to provide an image management system and image management method that can manage a plurality of images with a single image ID.

In order to solve the above described problem, an image management system according to this invention comprises:

input means that inputs a first image;

storage means that stores the first image;

registration decision means that decides whether or not a second image with attendant information that is the same as attendant information of the first image is registered in the system;

first registration means that registers the attendant information of the first image in association with the first image when the second image is not registered in the system; and second registration means that, when the second image is registered in the system and the attendant information of the second image is registered, registers information indicating that the first image is registered.

Further, in order to solve the above described problem, an image management method according to this invention has:

an input step for inputting a first image into an image management system;

a storage step for storing the first image in the image management system;

a decision step for deciding whether or not a second image with attendant information that is the same as attendant information of the first image is registered in the image management system;

a first registration step for registering the attendant information of the first image in association with the first image when the second image is not registered in the image management system; and a second registration step for registering information indicating that the first image is registered, when the second image is registered in the image management system and the attendant information of the second image is registered.

Further, in order to solve the above described problem, a program according to this invention causes a computer to execute:

an input procedure that inputs a first image;

a storage procedure that stores the first image;

a decision procedure that decides whether or not a second image with attendant information that is the same as attendant information of the first image is registered;

a first registration procedure that registers the attendant information of the first image in association with the first image when the second image is not registered; and a second registration procedure that registers information indicating that the first image is registered, when the second image is registered and attendant information included in the second image is registered.

Other feature and advantages of the present invention will be apparent from the following description taken in conjunction with the accompanying drawings, in which like references characters designate the same or similar parts throughout the figures thereof.

BRIEF DESCRIPTION OF THE DRAWINGS

The accompanying drawings, which are incorporates in and constitute a part of the specification, illustrate embodiments of the invention and, together with the description, serve to explain the principle of the invention.

FIG. 5 is a view showing an example of a table which stores attendant information of an image in an image attendant information holding part 206 according to one embodiment of this invention;

FIG. 6 is a view showing a table when an image before processing (original image) represented by an image ID "421580" was received after the state of the table shown in FIG. 5; and FIG. 7 is a view showing the appearance of a table when a processed image was further received following the state of the table shown in FIG. 6.

DETAILED DESCRIPTION OF THE PREFERRED EMBODIMENTS

Figure 1:
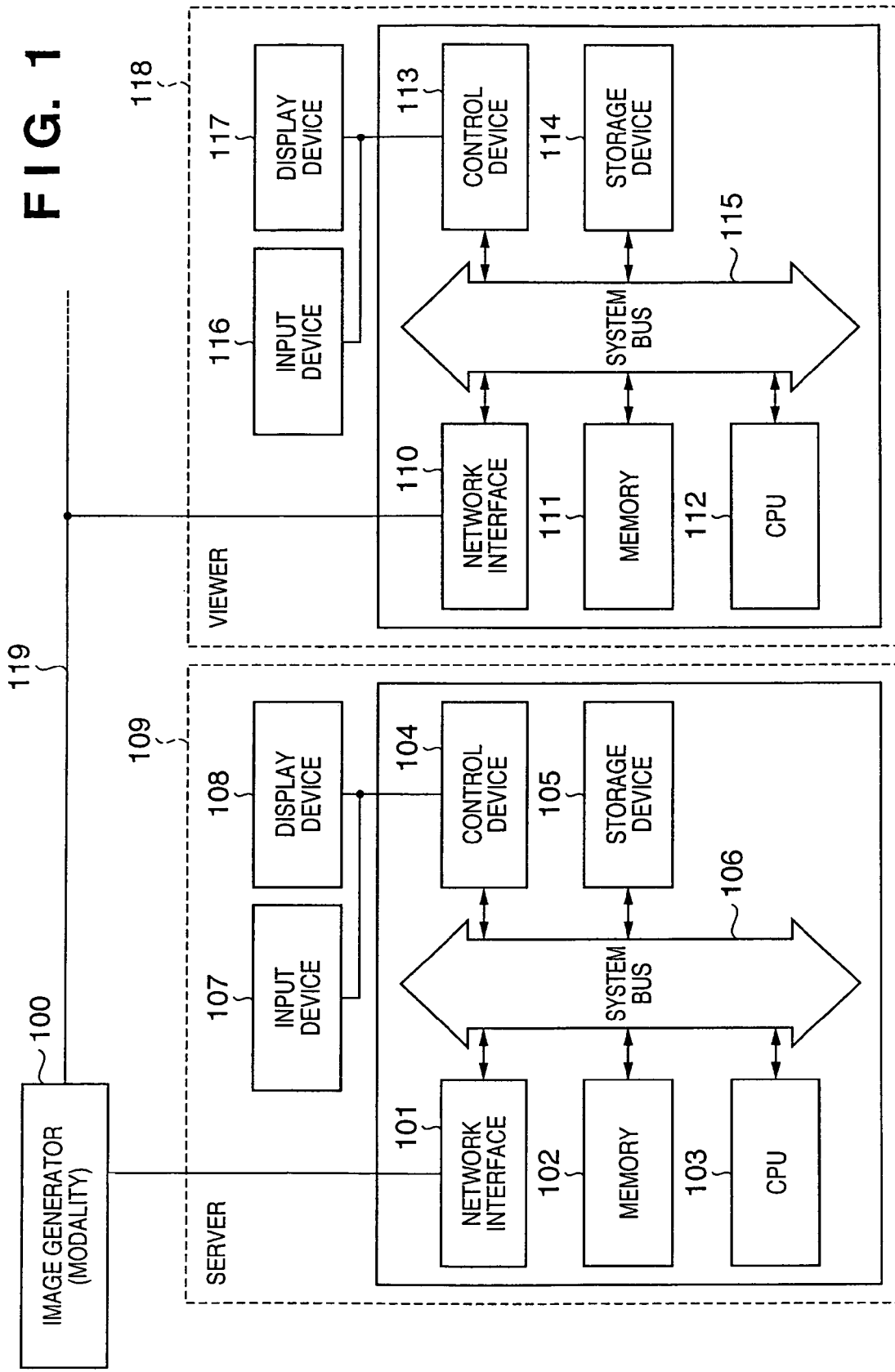
FIG. 1 is a hardware configuration diagram of an image management system that performs medical image management according to the first embodiment of this invention.

Hereunder, the image processing system according to this invention that can manage medical images and favorably reduce the occurrence of artifacts when generating a difference image is described in detail referring to the drawings.

First Embodiment

FIG. 1 is a hardware configuration diagram of an image management system that performs medical image management according to the first embodiment of this invention. In FIG. 1, reference numeral 100 denotes an image generator that performs radiation (for example, X-ray) imaging to generate an image. The image generator 100 is equipped with a common configuration (for example, a radiation generator or radiation sensor) for performing radiation imaging.

In the image management system shown in FIG. 1, the image generator 100 is connected with a server 109 through a network 119. The server 109 acts as an image server for accumulating and managing medical image data that was generated by the image generator 100 in the image management system of this embodiment. The server 109 has a so-called computer function, and comprises a configuration in which a network interface 101 for conducting communication with an external network, a memory 102, a CPU 103, a display device 108 that is realized by a CRT or a liquid crystal display, an input device 107 such as a mouse or keyboard, a control device 104 that controls the display device 108 and input device 107, and a storage device 105 that can be configured using a hard disk or a floppy disk or the like are connected through a system bus 106 to enable communication with each other.

Further, a viewer 118 for displaying accumulated (stored) images is connected to the server 109 through a network 119. The viewer 118 also has a computer function, and comprises a configuration in which a network interface 110 for conducting communication with an external network, a memory 111, a CPU 112, a display device 117 that is realized by a CRT or a liquid crystal display, an input device 116 such as a mouse or keyboard, a control device 113 that controls the display device 117 and input device 118, and a storage device 114 that can be configured using a hard disk or a floppy disk or the like are connected through a system bus 115 to enable communication with each other.

Figure 2:
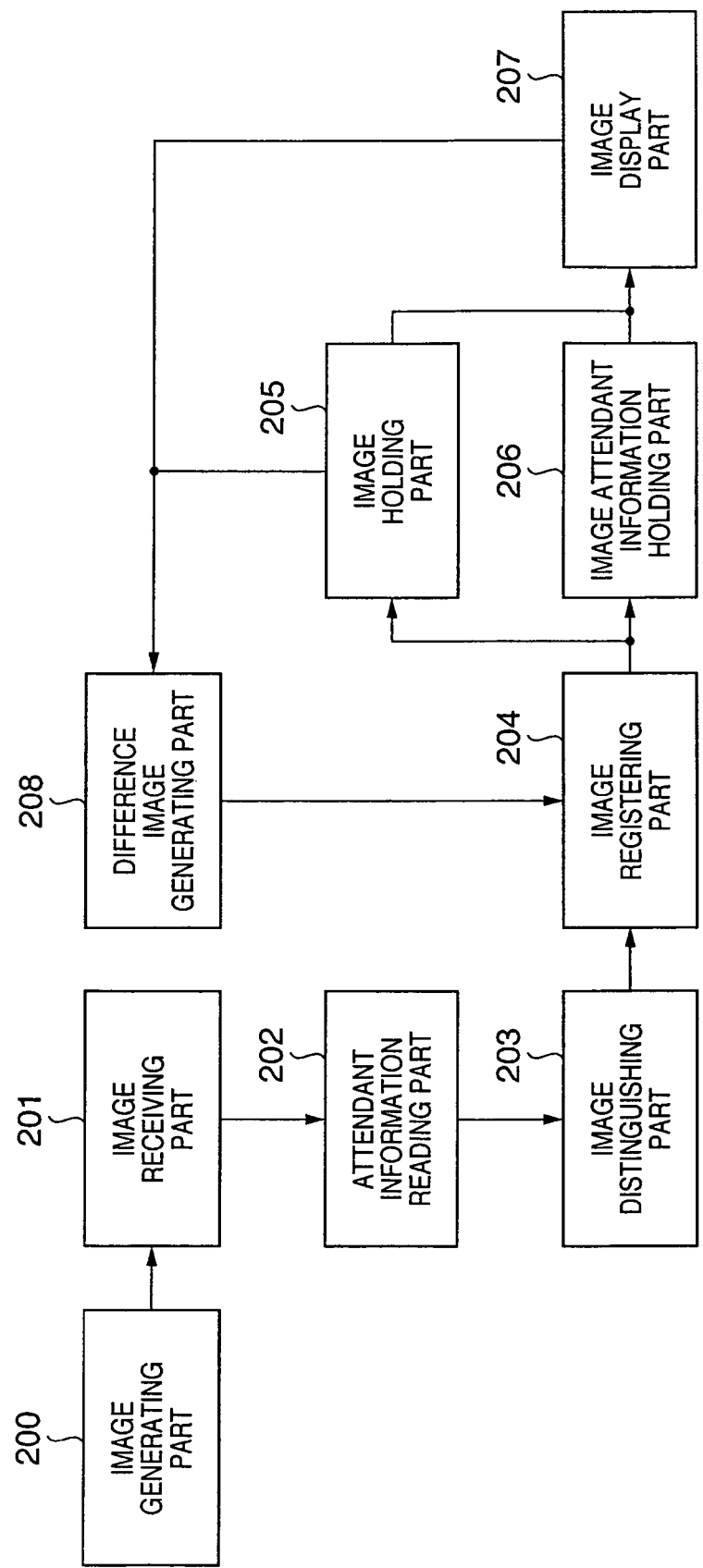
FIG. 2 is a block diagram for explaining the functions of the image management system according to the first embodiment comprising the hardware configuration shown in FIG. 1.

Next, the functions and configuration of the radiation image display of the first embodiment will be described using FIG. 2. FIG. 2 is a block diagram for explaining the functions of the image management system according to the first embodiment comprising the hardware configuration shown in FIG. 1.

In FIG. 2, an image generating part 200 corresponds to the image generator 100. The image generating part 200 can send not only an original image that was simply imaged and generated (that is, original images prior to optimization processing), but also an optimized image that was subjected to various kinds of optimization processing for radiogram interpretation observation. Although the image generator 100 is a device that outputs an original image and an optimized image, respectively, depending on the instruction of the operator in some cases only an original image or only an optimized image is output.

An image receiving part 201 is included in the server 109, and it receives an image (original image or optimized image) that was generated by the image generator 100 through the network 109. An attendant information reading part 202 reads the attendant information of an image received by the image receiving part 201. In this case, the term "attendant information" refers to information other than the image data such as, for example, the name of the patient that is the subject of the imaged image, the patient ID, imaging conditions, classification (information indicating whether the image is an original image or optimized image), and image ID (described in detail later).

An image distinguishing part 203 distinguishes the classification of image data received by the image receiving part 201, based on attendant information that was read by the attendant information reading part 202. More specifically, the image distinguishing part 203 can distinguish whether an image received by the image receiving part 201 is an image that is optimized for radiogram interpretation observation (optimized image) or is an image that did not undergo optimization processing (original image).

An image registering part 204, copies or moves image data received by the image receiving part 201 to an image holding part 205. The image registering part 204 not only copies or moves image data, but also performs processing to register attendant information that was read by the attendant information reading part 202 in an image attendant information holding part 206.

The functions of the aforementioned image receiving part 201, attendant information reading part 202, image distinguishing part 203, and image registering part 204 are realized using programs stored in the storage device 105 of the server 109, and these programs are executed by the CPU 103. The image holding part 205 is realized by a hard disk or the like constituting the storage device 105. Further, the image attendant information holding part 206 generally denotes a database located in the storage device 105, and it is a device that stores attendant information of an image as relational data.

Meanwhile, an image display part 207 in FIG. 2 reads out and displays an image stored in the server 109. The image display part 207 is generally a medical image viewer for enabling a radiogram interpreter to display a medical image and perform diagnosis. A difference image generating part 208 generates a difference image in accordance with an instruction from the image display part 207. The difference image generating part 208 is configured by an executable program, and while it may be located in either the server 109 or the viewer 118, a difference image that is generated by the difference image generating part 208 is preferably stored in the server 109.

Figure 3:
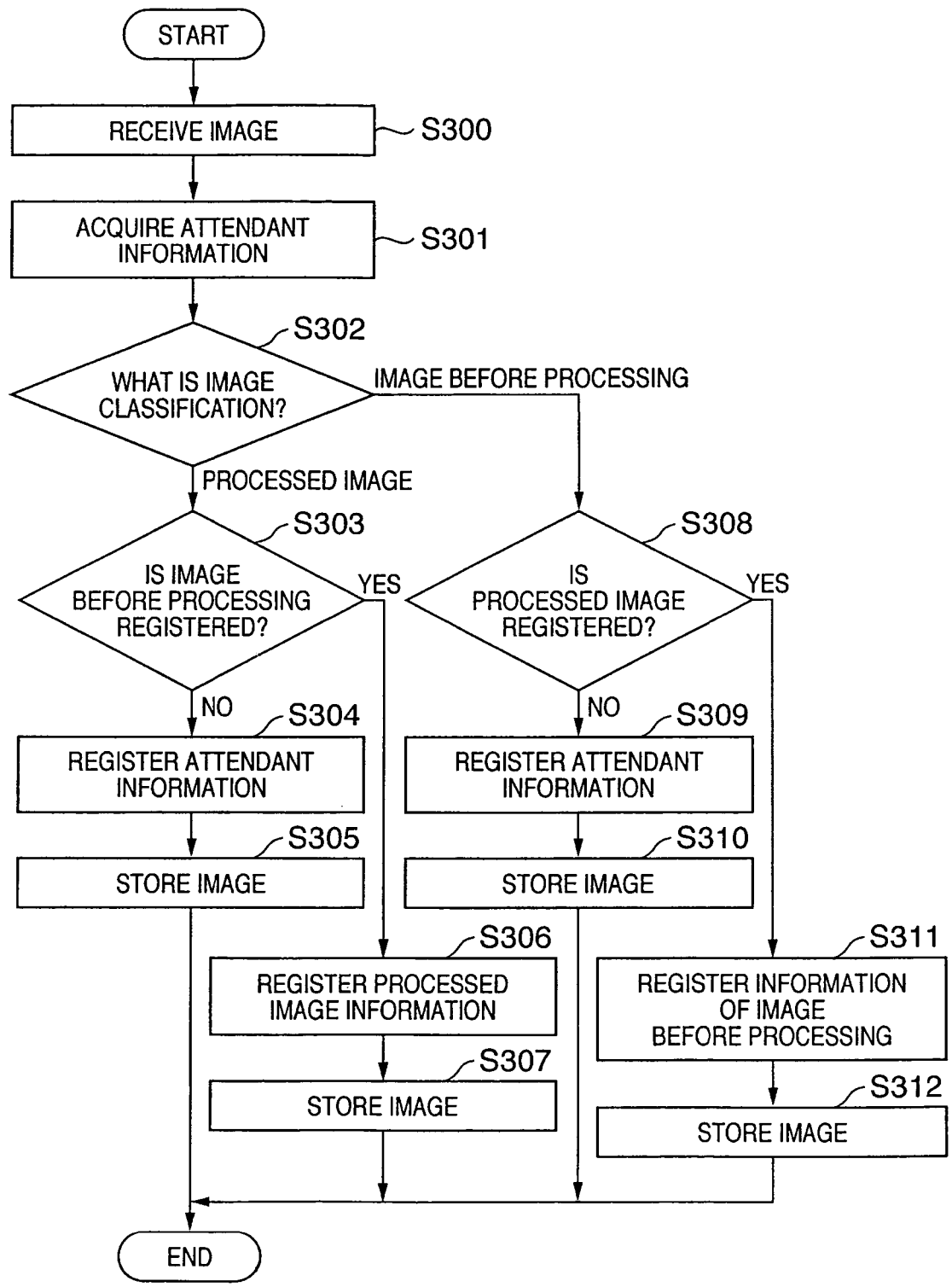
FIG. 3 is a flowchart for explaining processing operations from reception of an image to storage thereof at a server 109 in the image management system according to the first embodiment of this invention.

Next, the flow of operations of the medical image management system of the first embodiment will be described using FIG. 3. FIG. 3 is a flowchart for explaining processing operations from reception to storage of an image in the server 109 in the image management system according to the first embodiment of this invention. The flow of operations of the viewer 118 will be described later.

First, the image receiving part 201 of the server 109 receives an image generated by the image generator 100 (more specifically, either an optimized image or an original image) via the network 119 (step S300). Next, the attendant information reading part 202 reads attendant information that was attached to the received image (step S301). In this example, as described in the foregoing the term "attendant information" refers to patient information (for example, patient name, patient ID or the like), the imaging conditions when imaging the patient, or information that is unique to the imaging apparatus or the like that is written in a header region of the image.

Next, based on the attendant information that was read in step S301, the classification of the image is distinguished to determine whether or not the received image has undergone optimization processing to make the image suitable for radiogram interpretation (step S302). When it is determined as a result that the received image is an optimized image that has undergone optimization processing, the operation proceeds to the processing of step S303. In contrast, when it is determined that the received image is an original image that has not yet undergone optimization processing, the operation moves to the processing of step S308. This distinguishing processing is performed by the image distinguishing part 203.

In step S303, it is determined whether or not the original image as the pre-optimization image of the optimized image received in step S300 is already registered in the image management system. When it is determined as a result that the corresponding original image is not registered (No), the operation moves to step S304, and when it is determined that the corresponding original image is registered (Yes) the operation moves to step S306.

In this case, the original image as the object for determining whether or not an image is registered is an image having the same image ID as the image ID of the received optimized image. This image ID is an ID that the image generator 100 allocates to an image at the time of image generation, and there is no change in the image ID before and after optimization processing. For example, according to the DICOM standard that is widely used as a format for medical images, an ID in the form of a SOP instance UID can be utilized. More specifically, in step S303 it is determined whether or not image data of an original image that has not undergone optimization processing suited for radiogram interpretation which has the same image ID as the received optimized image is already registered in the database.

When an original image that has the same image ID as the received optimized image that underwent optimization processing was already registered in the database, an error may be generated without performing the registration described later or processing may be performed to overwrite the image by performing predetermined processing in accordance with the settings of an application.

When it is determined as a result of the processing of step S303 that an original image corresponding to the received optimized image is not registered in the image management system, the image registering part 204 registers the attendant information that was read from the optimized image in the database in the form of the image attendant information holding part 206 (step S304). The image registering part 204 subsequently stores the received optimized image in the image holding part 205 (step S305). In this connection, a description is provided later regarding association of the image stored in the image holding part 205 with the attendant information stored in the image attendant information holding part 206.

In contrast, when it is determined in step S303 that the original image prior to optimization processing is already registered (Yes), the operation moves to step S306. In step S306, because the attendant information of the original image was already registered together with the original image at the time of registration thereof, only the fact that the optimized image that underwent optimization processing was received is written to the database. More specifically, since an image before processing (original image) with the same ID is already registered, even if the attendant information is registered again it will only result in the writing of duplicated information. Therefore, in order to associate images having the same ID while eliminating that kind of wasteful operation, only flag information to the effect that a processed image was input is written to the database. After the processing of step S306, similarly to step S305 the image registering part 204 stores the received optimized image in the image holding part 205 that is realized by a hard disk or the like (step S307).

Next, the processing of step S308 and after will be described. As described in the foregoing, when the classification of a received image is determined in step S302 to be that of an image before optimization processing, the operation moves to step S308. In step S308, it is determined whether or not an image (optimized image) which underwent optimization processing suitable for radiogram interpretation is already registered in the database managed by the present image management system. When it is determined as a result that an image is not registered (No), the operation moves to step S309, and when it is determined that an image is registered (Yes), the operation moves to step S311.

In step S309, similarly to the above described step S304, attendant information that was read from the received original image is registered in the image attendant information holding part 206, and the operation moves to step 310. In contrast, in step S311, since an optimized image that was obtained by optimization of the received original image is already registered in the database, only the fact that the original image prior to optimization processing was received is written to the database using flag information, and the operation then moves to step S312. In both step S310 and step S312, processing is carried out to store the received original image in the image holding part 205.

Thus, the image receiving part 201 repeats the above described processing each time it receives an image from the image generating part 200.

Figure 4:
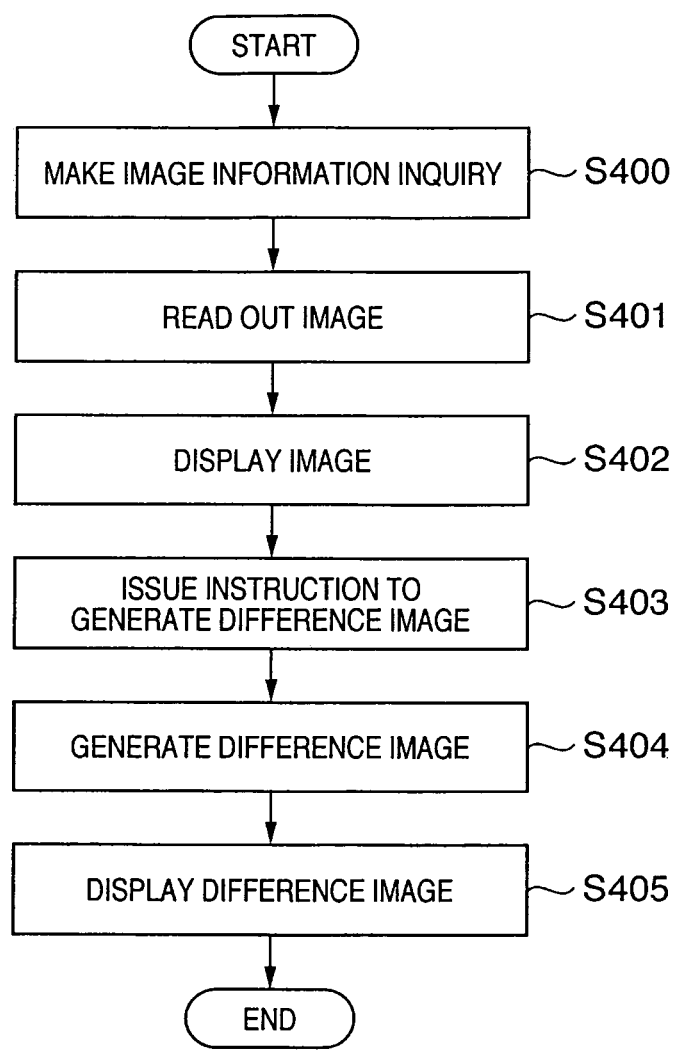
FIG. 4 is a flowchart for explaining processing operations from reading of an image to generation and display of a difference image at a viewer 118 in the image management system according to the first embodiment of this invention.

Next, the flow of operations of the viewer 118 in the image management system that manages medical images according to the first embodiment will be described. FIG. 4 is a flowchart for explaining processing operations from reading of an image to generation and display of a difference image at the viewer 118 in the image management system according to the first embodiment of this invention.

First, an image information inquiry is made at the viewer 118 (step S400). For example, based on the ID of a desired patient that was input by an operation of the radiogram interpreter, a search is executed in the image attendant information holding part 206 as the database. The storage location of images is written in this database, and based on this information an image that matches the search conditions is read from the image holding part 205 via the network 119 (step S401).

Subsequently, the image that was read in step S401 is displayed on the display device 117 of the viewer 118 (step S402). In this connection, when a plurality of images match the search conditions, the matching images are displayed in list form to allow selection of an image to be displayed from that list, or a configuration may also be adopted that displays a list of the matching images. An image is thus selected as an object for radiogram interpretation. The displayed image is an optimization processing image, and the image displayed at this time is used for diagnosis by the radiogram interpreter. Next, an instruction to generate a difference image is sent to the difference image generating part 208 (step S403) based on an operation by the radiogram interpreter. For example, the radiogram interpreter inputs an instruction by clicking on a command button (not shown) displayed on the viewer 118 using an input device such as a mouse. When making this instruction for a difference image, the radiogram interpreter specifies information to indicate which image and which other image the difference image is to be generated for, for example, in a state in which the radiogram interpretation images are displayed or, alternatively, the radiogram interpreter switches to the display list of images and specifies the target images from the display list.

Subsequently, the difference image generating part 208 generates a difference image in accordance with the instruction made in step S403 (step S404). Next, the difference image generated in step S404 is displayed on the viewer (step S405) and utilized for comparison radiogram interpretation. In this connection, the difference image generated in step S404 may be used for temporary display on the viewer 118, or may be delivered for processing to the image registering part 204 to undergo processing for registration to the database.

Although an image that underwent optimization processing for radiogram interpretation is generally displayed on the viewer 118, in many cases an optimized image is not an image that is suitable for differential processing, as described in the foregoing. Thus, by using images which have not been subjected to optimization processing for radiogram interpretation (that is, original images) when performing differential processing, it is possible to obtain an image with still fewer artifacts. Therefore, when generating a difference image, the difference image is generated using original images that have not been subjected to optimization processing as the reference images. Next, an image management method for realizing this mechanism will be described in detail.

FIG. 5 is a view showing an example of a table which stores attendant information of an image in the image attendant information holding part 206 according to one embodiment of this invention. Information relating to three images is held in the table shown in FIG. 5. In FIG. 5, an image ID 51 is an identification ID for uniquely specifying a stored image. The image ID 51 is written in the header region of the image. Further a processed 52 column and a before processing 53 column indicate, with the use of flags, whether or not an image that underwent optimization processing for radiogram interpretation and an image that did not undergo optimization processing are registered. For example, when an image that underwent optimization is registered, "1" is shown in the column for processed 52. Further, a path 54 represents a physical file name to indicate where in the image holding part 205 the image exists. The viewer uses the path 54 to acquire an image. Since the form for representing the file name is a common one, a detailed description thereof is omitted herein.

In this connection, the file name of a processed image (optimized image) is desirable for the physical file name to be written in the path 54. This is because an image that is generally displayed with the viewer 118 is a processed image. The example shown in FIG. 5 illustrates a case in which an image before processing (original image) and a processed image (optimized image) have the same image ID. More specifically, a case is assumed in which a processed image and an image before processing that have the same image ID are transferred from the image generator 100. In this case, patient information or examination information or the like is registered in the database using attendant information of the previously received image.

FIG. 6 is a view showing a table in a case where an image before processing (original image) represented by an image ID "421580" was received subsequent to the state of the table shown in FIG. 5. According to this embodiment, as shown in an attendant information 61 relating to the image ID "421580", in order to show that an image before processing (original image) was received, "1" is written as a flag in the before processing column (the flag is set). In contrast, when a processed image (optimized image) has not yet been registered, "0" is written in the processed column. In this connection, in FIG. 6, although nothing is written in the path, this is because, as described above, the physical file name to be written in the path is preferably the file name of a processed image (optimized image). However, by adopting a configuration whereby a processed image and an image before processing are associated to make it possible to easily refer to either image, any kind of physical file name may be used.

FIG. 7 is a view showing the appearance of a table when a processed image (for example, a processed image (optimized image) attached with an image ID "421580") was further received subsequent to the state of the table shown in FIG. 6. In FIG. 7, in order to indicate that a processed image attached with the image ID "421580" was received, "1" is written in the processed column for an image represented by attendant information 71. Further, the physical file name of a processed image is written in the path column for the image in question. As described in the foregoing, the physical file name of an image before processing is preferably held in association with the physical file name of the processed image. For example, by following a uniform file naming convention, such as employing the file name "421580_raw.dcm" for the image before processing of the image ID "421580" (in this example, a specific character string is only added to the physical file name of a processed image), it is possible to associate the image before processing with the processed image that has the same ID.

In this connection, in addition to associating an image before processing and a processed image using file names as in the above described example, the physical file name of the image before processing may be managed in a database, and any method may be used as long as it is a method that can associate an image before processing and a processed image.

As described in the foregoing, by associating and managing an image (optimized image) that underwent processing suitable for radiogram interpretation and an image (original image) that was not processed, it is possible to properly use the images in accordance with the purpose of use of an image such as for radiogram interpretation or differential processing. Further, a difference image with few artifacts can be obtained by performing differential processing using an original image without performing differential processing using an image for radiogram interpretation. More specifically, according to the image management system of this embodiment, it is possible to eliminate the labor involved in performing image processing to conduct differential processing again for an image that underwent optimization processing for radiogram interpretation. It is also possible to solve the problem that artifacts occur in a generated difference image due to differences in brightness values or density values. Furthermore, when obtaining a difference image, the original image under management can be used without the necessity to perform image processing to conduct differential processing based on an optimized image, making it thereby possible to shorten the processing time.

Second Embodiment

In the above described first embodiment, the server 109 and the viewer 118 were respectively connected in a singular manner through a network 119 to form an image management system. In contrast thereto, a configuration mat also be adopted in which a plurality of viewers are connected to the server 109 through the network 119. In this case, although each viewer carries out the operations described in the aforementioned first embodiment, an instruction to designate which of the viewers to display a difference image or optimized image or the like on is implemented by adding this processing to the processing of the image management system according to the first embodiment.

Third Embodiment

Although in the above described first embodiment the server 109 and the viewer 118 were respectively connected in a singular manner through a network 119, a configuration may be adopted in which the server 109 and the viewer 118 are both provided within the same information terminal device. At that time, the information terminal device in question will have a function that combines the respective functions of the server 109 and the viewer 118.

Fourth Embodiment

In an image management system configured as described in each of the above embodiments, a configuration may be adopted whereby, when issuing a difference image generation instruction from the viewer 118, either an image that underwent optimization processing for radiogram interpretation or an unprocessed image is selected to enable generation of a difference image from either image.

Fifth Embodiment

Although according to an image management system described in each of the above embodiments the server 109 acquires an image from the image generator 100 to which it is connected via the network 119, processing that is equivalent to the aforementioned processing can also be performed by reading an image from an offline storage device such as an MO or DVD or the like without being acquired via the network 119. For example, a configuration according to this embodiment may be employed in a case where the image generator 100 is provided in a diagnosis bus and cannot communicate directly with a server in a hospital. The configuration is this case will be one in which the image receiving part 201 shown in FIG. 2 reads an image from an offline media, without receiving an image directly from the network 119.

Sixth Embodiment

With respect to the aforementioned image management system, when receiving an image produced by the image generator 100, a configuration may be adopted whereby an image that was subjected to image processing to form an image suitable for radiogram interpretation observation (optimized image) and an image prior to the performance of processing (original image) are received in respectively different servers. More specifically, a processed image server and a server for images before processing are separately provided, and each server manages images independently. At this time, when displaying an image in a normal manner using the viewer 118, an optimized image is displayed by referring to the processed image server, and when displaying a difference image a difference generation instruction is sent to the server for images before processing to display a difference image that was created using the original image.

Other Embodiment

Although examples of embodiments of the present invention were described in detail above, this invention can also take the form of, for example, a system, an apparatus, a method, a program or a storage medium (recording medium). More specifically, the present invention can be applied to a system constituted by a plurality of devices or to an apparatus comprising a single device.

Note that the invention may also be accomplished by supplying a software program (a program corresponding to a flowchart shown in a figure according to the embodiments) which implements the functions of the foregoing embodiments directly or indirectly to a system or apparatus, reading the supplied program code with a computer of the system or apparatus, and then executing the program code.

Accordingly, since the functional processes of the present invention are implemented by computer, the program code itself installed in the computer also implements the present invention. In other words, the claims of the present invention also cover a computer program itself for the purpose of implementing the functional processes of the present invention.

In this case, so long as the system or apparatus has the functions of the program, the program may be executed in any form, e.g., as object code, a program executed by an interpreter, or script data supplied to an operating system.

Examples of recording media that can be used for supplying the program are a floppy (registered trademark) disk, a hard disk, an optical disk, a magneto-optical disk, an MO, a CD-ROM, a CD-R, a CD-RW, a magnetic tape, a non-volatile type memory card, a ROM, and a DVD (a DVD-ROM and a DVD-R).

As for the method of supplying the program, a client computer can be connected to a website on the Internet using a browser of the client computer, and the computer program of the present invention or an automatically-installable compressed file of the program can be downloaded to a recording medium such as a hard disk. Further, the program of the present invention can be supplied by dividing the program code constituting the program into a plurality of files and downloading the files from different websites. In other words, a WWW (World Wide Web) server that downloads, to multiple users, the program files that implement the functional processes of the present invention by computer is also covered by the claims of the present invention.

Further, it is also possible to encrypt and store the program of the present invention on a storage medium such as a CD-ROM, distribute the storage medium to users, allow users who meet certain requirements to download decryption key information from a website via the Internet, and allow these users to decrypt the encrypted program by using the key Information, whereby the program is installed in the user computer.

Furthermore, besides the case where the aforesaid functions according to the embodiments are implemented by executing the read program by computer, an operating system or the like running on the computer may perform all or a part of the actual processing based on the instructions of the program so that the functions of the foregoing embodiments can be implemented by this processing.

Furthermore, after the program read from the recording medium is written to a function expansion board inserted into the computer or to a memory provided in a function expansion unit connected to the computer, a CPU or the like mounted on the function expansion board or function expansion unit performs all or a part of the actual processing based on the instructions of the program so that the functions of the foregoing embodiments can be implemented by this processing.

As described in the foregoing, according to the present invention it is possible to favorably manage images for performing display of images that underwent optimization processing or for generating and displaying difference images in which the occurrence of artifacts was inhibited.

As many apparently widely different embodiments of the present invention can be made without departing from the spirit and scope thereof, it is to be understood that the invention is not limited to the specific embodiments thereof except as defined in the appended claims.

This application claims the benefit of Japanese Application No. 2005-112654, filed Apr. 8, 2005, which is hereby incorporated by reference herein in its entirety.

What is claimed is:

1. An image management system for performing subtraction between two images of the same patient, comprising:
   an input unit that inputs a first image which is one of a processed image type for displaying the first image on a monitor and an unprocessed original image type;
   a registration decision unit that decides whether or not a second image having image identification information that is the same as image identification information of the first image is registered in the image management system, wherein if the first image is the processed image type, the registration decision unit decides whether a second image that is the unprocessed original image type and has image identification information that is the same as image identification information of the first image is registered, and if the first image is the unprocessed original image type, the registration decision unit decides whether a second image that is the processed image type and has image identification information that is the same as image identification information of the first image is registered;
   a first registration unit that creates a new entry in a database for the first image and registers the image identification information of the first image in association with the first image in a case where the second image is not registered in the image management system, and stores the first image in a storage unit; and
   a second registration unit that, in a case where the second image is registered in the image management system in an existing entry in the database and the image identification information of the second image is registered in the existing entry, updates in the existing entry for the second image, information indicating that the input first image is now registered, and stores the first image in the storage unit.

2. The image management system according to claim 1, further comprising an image decision unit, wherein the image decision unit decides whether or not the first image has undergone optimization processing to make the first image into an image that is suitable for radiogram interpretation observation in image units.

3. The image management system according to claim 1, wherein a relationship between the first image and the second image is a relationship between an image that is generated by a specific image generator and an image obtained by performing image processing for the image, respectively.

4. The image management system according to claim 1, wherein the input unit inputs through a network the first image that is generated by a specific image generator.

5. The image management system according to claim 1, wherein the input unit reads and inputs the first image that is generated by a specific image generator and stored on a transportable storage medium.

6. The image management system according to claim 1, wherein the registration decision unit decides whether or not the second image that includes identification information that is the same as identification information allocated by an image generator that generated the first image which is included in the image identification information of the first image is registered in the system.

7. An image management method executed in an image management system for performing subtraction between two images of the same patient, the method comprising:
   the following steps executed by a computer processor of the image management system,
   an input step of inputting a first image which is one of a processed image type for displaying the first image on a monitor and an unprocessed original image type;
   a registration decision step of deciding whether or not a second image having image identification information that is the same as image identification information of the first image is registered in the image management system, wherein if the first image is the processing image type, the registration decision step decide whether a second image that is the unprocessed original image type and has image identification information that is the same as image identification information of the first image is registered, and if the first image is the unprocessed original image type, the registration decision step decides whether a second image that is the processed image type and has image identification information that is the same as image identification information of the first image is registered;

a first registration step of creating a new entry in a database for the first image and registering the image identification information of the first image in association with the first image in a case where the second image is not registered in the image management system, and storing the first image in a storage unit; and a second registration step of, in a case where the second image is registered in the image management system in an existing entry in the database and the image identification information of the second image is registered in the existing entry, updating the existing entry for the second image with information indicating that the input first image is now registered, and storing the first image in the storage unit.

8. A non-transitory computer-readable storage medium on which is stored a computer-executable program which causes an image management system for performing subtraction between two images of the same patient to execute an image management method, said program comprising:

code for an input step of inputting a first image which is one of a processed image type for displaying the first image on a monitor and an unprocessed original image type;

code for a registration decision step of deciding whether or not a second image having image identification information that is the same as image identification information of the first image is registered in the image management system, wherein if the first image is the processed image type, the registration decision step decides whether a second image that is the unprocessed original image type and has image identification information that is the same as image identification information of the first image is registered, and if the first image is the unprocessed original image type, the registration decision step decides whether a second image that is the processed image type and has image identification information that is the same as image identification information of the first image is registered;

code for a first registration step of creating a new entry in a database for the first image and registering the image identification information of the first image in association with the first image in a case where the second image is not registered in the image management system, and storing the first image in a storage unit; and code for a second registration step of, in a case where the second image is registered in the image management system in an existing entry in the database and the image identification information included in the second image is registered in the existing entry, updating the existing entry for the second image with information indicating that the input first image is now registered, and storing the first image in the storage unit.

* * * * *